United States Patent [19]

Onodera et al.

[11] 4,320,242

[45] Mar. 16, 1982

[54] PROCESS FOR SELECTIVE DEALKYLATION OF ALKYL-SUBSTITUTED AROMATIC HYDROCARBONS

[75] Inventors: Tamio Onodera; Tokuji Sakai; Yasuo Yamasaki; Koji Sumitani, all of Matsuyama; Minekazu Sueoka, Hino, all of Japan

[73] Assignee: Teijin Petrochemical Industries Ltd., Tokyo, Japan

[21] Appl. No.: 118,324

[22] Filed: Feb. 4, 1980

[30] Foreign Application Priority Data

Sep. 21, 1979 [JP] Japan .................................. 54-120805

[51] Int. Cl.$^3$ ................................................ C07C 4/12
[52] U.S. Cl. ...................................... 585/489; 208/111
[58] Field of Search ................ 585/489, 486, 487, 488; 208/111

[56] References Cited

U.S. PATENT DOCUMENTS 4,101,595  7/1978  Chen et al. ........................... 585/481

*Primary Examiner*—Curtis R. Davis
*Attorney, Agent, or Firm*—Sherman & Shalloway

[57] ABSTRACT

In a process for dealkylating a hydrocarbon material containing at least one alkyl-substituted aromatic hydrocarbon having bonded to the aromatic ring at least one alkyl group with at least 2 carbon atoms in the gaseous phase in the presence of hydrogen using a hydro-dealkylation catalyst, the improvement wherein (a) said hydro-dealkylation catalyst is composed of a crystalline aluminosilicate having a silica/alumina mole ratio of from 20 to 200 and containing a noble metal selected from platinum, palladium, rhodium and iridium, and (b) said dealkylation is carried out at a temperature of 250° C. to 420° C. and a pressure of not more than 100 psig, thereby selectively removing said alkyl group containing at least 2 carbon atoms from said alkyl-substituted aromatic hydrocarbon.

15 Claims, No Drawings

PROCESS FOR SELECTIVE DEALKYLATION OF ALKYL-SUBSTITUTED AROMATIC HYDROCARBONS

This invention relates to an improvement in a process for selectively dealkylating alkyl-substituted aromatic hydrocarbons. More specifically, it relates to a novel process for producing industrially more valuable aromatic hydrocarbons such as benzene, toluene and xylene by selectively dealkylating alkyl-substituted aromatic hydrocarbons having bonded to the aromatic ring at least one alkyl group with at least two carbon atoms, especially ethyl group-containing benzenes such as ethyltoluene, diethylbenzene and ethylxylene.

Among aromatic hydrocarbons now in commercial use, benzene, toluene and xylene (these three aromatic hydrocarbons may sometimes be referred to as "BTX") are most useful commercially in view of their supply and demand.

BTX is obtained conventionally by separating aromatic hydrocarbon components through solvent extraction, etc. from starting hydrocarbons such as catalytically reformed hydrocarbons and thermally cracked gasoline, and distilling the extract. High-boiling residues containing aromatic hydrocarbons having 9 or more carbon atoms which remain as bottoms after the separation of BTX in the conventional process are of low utilitarian value, and most of them have been used only as fuels.

On the other hand, to recover a maximum amount of p-xylene which is most valuable commercially from a $C_8$ fraction containing three isomers of xylene and optionally ethylbenzene (to be simply referred to as a $C_8$ fraction), it has been the previous practice to treat the $C_8$ fraction in the presence of an isomerization catalyst. In commercial practice, this technique involves a suitable combination of a step of isomerizing the $C_8$ fraction, a step of separating xylene isomers from the isomerization reaction mixture, and a step of recycling the remaining components left after the separation to the isomerization step. In the isomerization step, disproportionation of xylenes, disproportionation of ethylbenzenes, and trans-alkylation of xylenes and ethylbenzene take place in addition to the isomerization of xylenes which is a main reaction. These side-reactions yield a mixture of alkyl-substituted aromatic hydrocarbons having at least 9 carbon atoms ($C_9+$) such as ethyltoluenes, trimethylbenzenes, ethylxylenes and diethylbenzenes (this mixture may sometimes be referred to herein as a "heavy end").

If the aforesaid $C_9+$ alkyl-substituted aromatic hydrocarbon mixture can be converted effectively to commercially more valuable BTX by, for example, hydro-dealkylation, a great commercial advantage can be obtained in the process of manufacturing p-xylene because the yield of xylene increases. The value of the by-products also increases. Thus, such a converting method has been extensively investigated heretofore.

Various suggestions have been made in the past about catalyst compositions and/or treating conditions for this hydro-dealkylation treatment. For example, the following prior techniques can be cited.

(1) A $C_7$–$C_8$ alkyl aromatic hydrocarbon is dealkylated on a chromia-alumina catalyst at a temperature of at least 590° C. while maintaining the $H_2$/hydrocarbon mole ratio at 4 or more (British Pat. No. 959,609).

(2) A fraction containing alkyl aromatic hydrocarbons is hydrogenatingly dealkylated with a chromia-alumina catalyst in the presence of hydrogen and a small amount of sulfur at a temperature of 540° to 820° C. and a pressure of 20 to 68 atmospheres (Belgian Pat. No. 618,928).

(3) Aromatic hydrocarbons are produced by contacting a material containing a major proportion of aromatics having a boiling point of at least 220° F. with a ZSM-5 catalyst combined with a hydro-dehydrogenating component, in the presence of hydrogen at 500° to 1000° F. (260° to 538° C.) and about 100 to 600 psig while maintaining a weight hourly space velocity (WHSV) of 0.5 to 15 and a hydrogen/hydrocarbon mole ratio of from 1 to 6 (U.S. Pat. No. 3,948,758).

(4) $C_6$–$C_8$ aromatic hydrocarbons are produced without substantial formation of high-boiling aromatic hydrocarbons owing to disproportionation or alkyl-exchange reaction by contacting aromatic hydrocarbons having a higher molecular weight than $C_8$ aromatic hydrocarbon with a ZSM-5 catalyst in the presence of hydrogen at 550° to 1000° F. (288° to 538° C.) and about 100 to 2000 psig while maintaining a hydrogen/hydrocarbon mole ratio of from 0.5 to 10 and a WHSV of 0.5 to 200 (U.S. Pat. No. 3,945,913).

The hydro-dealkylation method in the presence of the catalyst described in the prior art has the general defect that it is carried out at a relatively high temperature (450° to 650° C.) and pressure (1 to 30 kg/cm$^2$·G); that side-reactions such as the condensation of the benzene ring and the hydrogenation of the benzene ring occur; and that the stability of the catalyst is poor.

The present inventors made various investigations in order to develop a method of hydro-dealkylation of alkyl-substituted aromatic hydrocarbons which is free from the above defects. These investigations have led to the discovery that when the hydro-dealkylation reaction is carried out by using a special zeolite containing a noble metal as a hydro-dealkylation catalyst at a relatively low temperature of 250° to 420° C. and a low pressure of not more than 100 psig, an alkyl-substituted aromatic hydrocarbon having bonded to the aromatic ring at least one alkyl group with at least 2 carbon atoms can be dealkylated in a high conversion with the selective elimination of alkyl groups containing at least 2 carbon atoms while maintaining any methyl group bonded to the aromatic ring intact and without substantially involving side-reactions such as disproportionation, trans-alkylation, the condensation of the benzene ring, or the hydrogenation of the benzene ring; and therefore, that when the aforesaid heavy end is subjected to hydro-dealkylation treatment under the aforesaid conditions, ethyltoluenes, ethylxylenes and diethylbenzenes contained in the heavy end are converted in high conversions to toluene, xylenes, benzene and ethylbenzene, respectively (trialkylbenzenes remain unreacted).

Thus, the present invention provides, in a process for dealkylating a hydrocarbon material containing at least one alkyl-substituted aromatic hydrocarbon having bonded to the aromatic ring at least one alkyl group with at least 2 carbon atoms in the gaseous phase in the presence of hydrogen using a hydro-dealkylation catalyst, the improvement wherein (a) said hydro-dealkylation catalyst is composed of a crystalline aluminosilicate having a silica/alumina mole ratio of from 20 to 200 and containing a noble metal selected from platinum, palladium, rhodium and iridium, and (b) said dealkylation is carried out at a temperature of 250° C. to 420° C. and a pressure of not more than 100 psig, thereby selectively removing said alkyl group containing at least 2 carbon atoms from said alkyl-substituted aromatic hydrocarbon.

According to the process of this invention, a catalyst composed of crystalline aluminosilicate having a silica/alumina mole ratio of from 20 to 200 and containing a noble metal selected from platinum, palladium, rhodium and iridium is used as the hydro-dealkylation catalyst.

The crystalline aluminosilicate (to be sometimes referred to as zeolite) forming the base of the catalyst used in this invention contains mainly hydrogen or a hydrogen precursor such as an ammonium ion at a cation site and has a silica/alumina mole ratio of from 20 to 200, preferably from 30 to 150, more preferably from 40 to 100. In other words, a so-called high-silica zeolite having a high content of silica relative to alumina is used as a base of the catalyst. Many zeolites having a high silica content relative to alumina have been suggested heretofore, and a zeolite having an extremely high silica content represented by a silica/alumina mole ratio of as high as 2,000 is also known. The present invention is characterized by the use of a high-silica zeolite which has a relatively low silica/alumina ratio and therefore, has a relatively high acid activity attributed to the alumina component. Conventional high-silica zeolite catalysts are used in a special way in order to reduce their acid activity, promote hydro-dealkylation of alkylbenzenes, especially monoalkylbenzenes, and inhibit side-reactions such as disproportionation and/or trans-alkylation. For example, the zeolite catalysts are used together with basic substances such as amines; or the zeolites are treated with steam, etc. to destroy part of their acid site, and used in the hydrodealkylation process at a high temperature of for example, more than 426.7° C. while shortening the time of contact of the feedstock with the catalyst (see, for example, U.S. Pat. No. 4,101,595).

Any known high-silica zeolites can be used in this invention if their silica/alumina mole ratio is within the above-specified range.

Typical examples of crystalline aluminosilicates or zeolites that can be used in this invention as a catalyst base include various ZSM series zeolites developed by Mobil Oil Corporation, and zeta-series zeolites developed by Imperial Chemical Industries, Ltd. The ZSM series zeolites are preferred.

Examples of ZSM-series zeolites are ZSM-5 (see U.S. Pat. No. 3,702,886), ZSM-11 (U.S. Pat. No. 3,709,979), ZSM-12 (see U.S. Pat. No. 3,832,449), ZSM-35 (see U.S. Pat. No. 4,016,245) and ZSM-38 (see U.S. Pat. Nos. 4,046,859 and 4,105,541). Examples of zeta-series zeolites are zeta 1 (see German Offenlegungsschrift No. 2,548,697), and zeta 3 (see German Offenlegungsschrift No. 2,548,695).

TP-1 series zeolites discovered by the present inventors as high-silica zeolites (see Japanese Laid-Open Patent Publication No. 137,500/79) can also be used. These TP-1 series zeolites are obtained by heating a starting mixture containing silica, alumina, alkali metals and water at a temperature and for a time sufficient for the formation of crystalline aluminosilicates by using organic sulfur compounds such as thiols, sulfides, sulfoxides, sulfones or thiophenes. The properties of these TP-1 series zeolites and their production are described in detail in the specification of the Japanese Laid-Open Patent Publication cited above.

These zeolites are generally available in a form containing an alkali metal ion or an alkaline earth metal ion at the cation site. In the present invention, these zeolites are converted to H-form zeolites, and used in the form containing mainly hydrogen or a hydrogen precursor at the cation site. Accordingly, unless otherwise specified, "zeolite", as used in the present application, denotes H-form zeolite.

It has been found that the use of ZSM-5 zeolite as a catalyst base produces the best effect. Thus, according to a preferred embodiment of the process of this invention, ZSM-5 zeolite is used as a base of the hydro-dealkylation catalyst.

In the process of this invention, the foresaid zeolite having a specified silica/alumina mole ratio is modified with a noble metal and used as a main catalyst ingredient. Experiments of the present inventors showed that when a high silica zeolite not modified with a noble metal is used directly as a catalyst in the hydro-dealkylation of an alkyl-substituted aromatic hydrocarbon, the alkyl group containing at least 2 carbon atoms such as an ethyl group bonded to the aromatic ring can be hydrogenated and dealkylated, but at the same time, demethylation reaction involving the elimination of the methyl group bonded to the aromatic ring tends to take place; and that because the unmodified high-silica zeolite does not have the hydrogenating ability, its activity gradually decreases with the deposition of a carbonaceous substance on long-term use.

It has, however, been found in accordance with this invention that when a zeolite modified with a noble metal is used as the hydro-dealkylation catalyst under the specific reaction conditions described above, dealkylation reaction involving the elimination of the methyl group bonded to the aromatic ring is greatly inhibited and side-reactions scarcely take place while dealkylation reaction of the alkyl substituent having at least 2 carbon atoms proceeds selectively, and that the activity of the catalyst does not appreciably decrease even when the catalyst is used continuously over a long period of time, and the active lifetime of the catalyst can be maintained long.

The noble metal used in the modification of zeolite is selected from platinum, palladium, rhodium and iridium. Platinum and palladium are preferred. Platinum is especially preferred because it brings about a high reaction selectivity and a great inhibiting action on the reduction of activity.

The term "modified with a noble metal", as used herein, means that the noble metal is ion-exchanged at the cation site of zeolite and/or the noble metal or a compound containing it is physically deposited on the surface of zeolite.

The zeolite modified with a noble metal can be prepared by a method known per se, for example by the method described in Example 9 of U.S. Pat. No. 3,856,872. To facilitate understanding, typical examples of the modifying method are described below in detail.

Commercially available zeolites generally have alkaline metal ions or alkaline earth metal ions such as Na, K or Ca substituted at the cation site thereof. Hence, the alkali metal or alkaline earth metal ion is exchanged with hydrogen or an ammonium ion. This exchange may be performed simultaneously with, or prior to, the modification with a noble metal.

One method comprises dipping a zeolite having its cation site substituted with an alkali metal or alkaline earth metal ion in an aqueous solution containing a noble metal ion and an ammonium ion to give a zeolite product which is modified with the noble metal and in which a greater portion of the cation site is of the ammonium ion form. Calcination of the resulting ammonium ion-form zeolite modified with the noble metal at a temperature of about 200° to 600° C. gives a hydrogen ion-form zeolite modified with the noble metal.

Another method comprises treating a zeolite having its cation site substituted with an alkali metal or alkaline earth metal ion with an inorganic or organic acid such as hydrochloric acid, sulfuric acid, nitric acid, acetic acid or oxalic acid to convert a greater portion of the cation site to a hydrogen ion form, and exchanging the hydrogen ion with a noble metal ion or depositing the noble metal on the resulting zeolite.

Still another method comprises treating a zeolite having its cation site substituted by an alkali metal or alkaline earth metal ion with an aqueous solution of a water-soluble ammonium compound to form a zeolite having a greater portion of its cation site substituted with an ammonium ion, which zeolite is then optionally converted to an H-form zeolite by calcination at a temperature of, for example, about 200° to about 600° C., and finally exchanging the ammonium ion or hydrogen ion with a noble metal ion, or depositing the noble metal on the ammonium ion-type or hydrogen ion-type zeolite. In this method, substitution by an ammonium ion can be easily carried out by contacting the zeolite with an aqueous solution of a water-soluble ammonium compound such as ammonium chloride or ammonium nitrate in a concentration of 5 to 20% by weight.

Ion exchange of zeolite with a noble metal and/or deposition of the noble metal on the zeolite can be performed by techniques known to be used in subjecting ordinary zeolites to ion exchange with noble metals or in depositing noble metals on such zeolites.

For example a zeolite to be treated is contacted with an aqueous or non-aqueous medium containing a compound of the desired noble metal dissolved therein. Such noble metal compounds include the halides, oxides, sulfides, oxy acid salts, and complexes. When it is desired to modify a zeolite with platinum, the zeolite may be impregnated with an aqueous solution of a water-soluble platinum compound (such as $H_2PtCl_6$, or $PtCl_2$) and then water is evaporated off to deposit platinum on the zeolite. Or the zeolite may be dipped in an aqueous solution of a platinum compound having ion exchange ability such as a platinum-ammine complex [e.g., $Pt(NH_3)_4Cl_2$], and then subjected to filtration, followed by sufficient washing. As a result, the zeolite is ion-exchanged with a platinum cation.

Prior to the modification treatment with a noble metal, zeolite may be heated for 1 to 50 hours in an oxygen atmosphere such as air or an inert gaseous atmosphere such as nitrogen at a temperature of 100° to 700° C., preferably 200° to 600° C. This generally gives better catalysts.

The zeolite modified with a noble metal may be heated in an oxygen-containing atmosphere such as air or an inert gaseous atmosphere such as nitrogen at a temperature of 100° to 700° C., preferably 200° to 600° C., for about 1 to about 5 hours. This heat-treatment is preferred in this invention.

The amount of the noble metal in the zeolite modified with the noble metal can be varied according to the type of the metal, etc., but may be smaller than in zeolite-type catalysts used conventionally in hydro-dealkylation. Advantageously, the noble metal is incorporated in an amount of generally 0.001 to 2% by weight, preferably 0.01 to 1% by weight, calculated as noble metal based on the weight of the zeolite. The optimal amount of the noble metal varies with the type of the metal. It is 0.001 to 0.5% by weight, especially 0.005 to 0.5% by weight, for platinum; and 0.05 to 2% by weight, especially 0.1 to 1% by weight, for palladium, rhodium and iridium, both based on the weight of the zeolite.

The resulting noble metal-modified zeolite can be used in hydro-dealkylation reaction either in the form of a fine powder, or after optionally shaping it into the various desired shapes such as pellets or tablets as is the case with the customary practice. A shaped articles of the modified zeolite can be obtained in a customary manner by mixing the modified zeolite with a synthetic or natural refractory inorganic oxide usually employed as a binder for zeolite-type catalysts, such as silica, alumina, silica-alumina, kaolin or silica-magnesia, shaping the mixture into the desired configuration, and then calcining the shaped article. Advantageously, the amount of the modified zeolite as an active catalyst ingredient in the shaped article is generally 1 to 99% by weight, preferably 10 to 90% by weight, based on the weight of the shaped article.

In use, the catalyst composed of zeolite modified with a noble metal prepared in the above-mentioned manner is treated in a reducing atmosphere such as a hydrogen gas at a temperature of 200° to 600° C., preferably 250° to 550° C. This reducing treatment is usually carried out after the catalyst has been filled in a reactor for hydrodealkylation.

The catalyst composed of a high-silica crystalline aluminosilicate containing a noble metal prepared in the above manner can be used as a hydro-dealkylation catalyst in dealkylating a hydrocarbon material containing at least one alkyl-substituted aromatic hydrocarbon in the vapor phase in the presence of hydrogen.

The process of this invention is characterized by the fact that the dealkylation reaction is carried out (i) at a relatively low temperature of 250° C. to 420° C., and (ii) at a relatively low pressure of not more than 100 psig.

When the dealkylation reaction is carried out under such mild temperature and pressure in the presence of the above catalyst, dealkylation of the alkyl-substituted aromatic hydrocarbon takes place selectively at the alkyl groups containing at least 2 carbon atoms, and the dealkylation of the methyl group bonded to the aromatic ring can be inhibited substantially completely. Moreover, side-reactions such as disproportionation and trans-alkylation of the alkyl-substituted aromatic hydrocarbon, and the hydrogenation of the aromatic ring can be effectively inhibited. It has been found therefore that the application of the process of this invention to the aforesaid heavy end can bring about a marked advantage in that commercially valuable BTX can be recovered in an extremely high yield.

The preferred temperature for the practice of the process of this invention is from 320° C. to 410° C., more preferably from 330° C. to 410° C., and the preferred pressure is 0 to 90 psig, more preferably 0 to 80 psig.

The starting hydrocarbon material used in the process of this invention contains at least one alkyl-substituted aromatic hydrocarbon having bonded to the aromatic ring at least one alkyl group having at least 2 carbon atoms. The hydrogen material may consist of only one alkyl-substituted aromatic hydrocarbon, or of two or more alkyl-substituted hydrocarbons, or of a mixture of at least one alkyl-substituted aromatic hydrocarbon and another aromatic hydrocarbon and/or an aliphatic and/or alicyclic hydrocarbon.

The alkyl-substituted aromatic hydrocarbon may contain as a substituent only a lower linear or branched alkyl group containing at least 2 carbon atoms, preferably 2 to 4 carbon atoms; or in addition to such an alkyl substituent, it may also contain a methyl group bonded to the aromatic ring. Examples of the alkyl substituent containing at least 2 carbon atoms include ethyl, n-propyl, isopropyl, n-butyl, isobutyl, sec.-butyl and tert.-butyl. The process of this invention can be applied with particular advantage to aromatic hydrocarbons containing an ethyl group as a substituent. The number of the alkyl substituents having at least 2 carbon atoms is not particularly limited. But generally, it is from 1 to 3, preferably 1 or 2. The number of methyl groups which may be present is neither restricted. If they are present, their number may be generally 1 to 5, especially 1 to 4. The aromatic ring to which these alkyl groups are bonded is usually a benzene ring.

Examples of the alkyl-substituted aromatic hydrocarbons to which the process of this invention can be advantageously applied include ethylbenzene, ethyltoluene, diethylbenzene, ethylxylene, n-propylbenzene, cumene, and cymene.

According to the process of this invention, these alkyl-substituted aromatic hydrocarbons are subjected to the hydro-dealkylation reaction generally as a mixture with other methyl-substituted aromatic hydrocarbons or further with an aliphatic and/or alicyclic hydrocarbon.

Specific examples of the other methyl-substituted aromatic hydrocarbons are methyl-substituted benzenes having 1 to 5 methyl groups bonded to the benzene ring, such as toluene, xylene, trimethylbenzene, and tetramethylbenzene.

The starting hydrocarbons material to be subjected to the process of this invention may contain the alkyl-substituted aromatic hydrocarbon in a concentration of at least 30% by weight, preferably at least 40% by weight, more preferably at least 50% by weight. Desirably, at least 80% by weight, preferably at least 90% by weight, of the starting hydrocarbon material consists of a mixture of the alkyl-substituted aromatic hydrocarbon containing alkyl groups with at least 2 carbon atoms with the methyl-substituted aromatic hydrocarbon.

Specific examples of the starting hydrocarbon include hydrocarbon mixtures containing alkyl-substituted aromatic hydrocarbons having a boiling point of at least 110° C., preferably at least 120° C., which are recovered from various processes such as a process of producing BTX from a reformed gasoline, a xylene isomerization process, and a process for producing BTX from a cracked gasoline. The process of this invention can be applied especially advantageously to a high-boiling fraction ("heavy end") containing large amounts of aromatic hydrocarbons having at least 9 carbon atoms and having a boiling point of at least 140° C., preferably at least 150° C., which is formed in the step of isomerizing xylene in the xylene manufacturing process.

It is also possible to treat mixed xylenes obtained from reformed and/or cracked gasolines in accordance with the process of this invention to obtain xylenes having a low ethylbenzene concentration, and to use them as starting materials for the production of p-xylene and/or o-xylene.

In the practice of the process of this invention, the starting hydrocarbon material is fed at a rate which can be varied widely according to the type of the hydrocarbon material used, the type of the catalyst, etc. Generally, it is advantageous to feed the hydrocarbon stock at a weight hourly space velocity of about 0.1 to about 20, preferably 0.2 to 15, more preferably 0.5 to 10.

In the present specification and appended claims, the "weight hourly space velocity" is a value calculated in accordance with the following equation.

$$\frac{\text{Weight of the starting hydrocarbon material fed per hour}}{\text{Weight of the catalyst}}$$

The "weight of the catalyst", as used herein, denotes the weight of crystalline aluminosilicate which forms the base of the catalyst.

The dealkylation reaction of this invention is carried out in the presence of hydrogen. The rate of feeding hydrogen in this case can be varied widely according to the type of the hydrocarbon material and/or the catalyst, etc. Generally, it is appropriate to feed hydrogen at such a rate that the hydrogen/hydrocarbon mole ratio is generally from 0.5 to 10, preferably from 1 to 8.

The process of this invention brings about the following excellent technical advantages over similar conventional techniques, and can contribute greatly to industry.

(1) In the present invention, only alkyl groups with at least 2 carbon atoms which are bonded to the aromatic ring selectively undergo dealkylation, and the hydro-dealkylation of methyl groups bonded to the aromatic ring does not substantially take place. Moreover, even when the hydrocarbon material is reacted at a high conversion, side-reactions such as the formation of naphthene by the hydrogenation of the aromatic ring, and trans-alkylation scarcely occur. Thus, the dealkylation of the alkyl groups with at least 2 carbon atoms can be achieved with a very high selectivity.

According to the process of this invention, therefore, aromatic hydrocarbons having at least 9 carbon atoms, such as ethyltoluene, ethylxylene or diethylbenzene which is contained in the heavy end discharged from the xylene isomerization step and being substantially valueless commercially as such can be converted to commercially valuable products such as toluene and xylene. The resulting toluene, xylene, etc. can be easily purified by a simple distillation procedure because the amounts of by-products such as naphthene are small.

(2) Because the reaction in the process of this invention is carried out at relatively low temperatures and low pressures, coke formation is very much reduced, and the active lifetime of the catalyst can be prolonged. Thus, the number of operations of catalyst regeneration can be drastically reduced.

(3) Under the reaction conditions in accordance with this invention, a secondary reaction of the alkyl group removed from the aromatic ring can be inhibited by the hydro-dealkylation. Accordingly, an alkane corresponding to the removed alkyl group and having the same number of carbon atoms as the removed alkyl group is formed quantitatively.

(4) Because the process of this invention is operated at relatively low reaction temperatures and pressures, costs required for the construction and maintenance of manufacturing facilities, energy consumption, etc. can be curtailed.

The following Examples illustrate the process of this invention more specifically. It should be noted however that the present invention is not limited to these examples.

EXAMPLE 1

(Preparation of Catalysts)

(a) Preparation of Catalyst A (H-type ZSM-5)

A zeolite was synthesized by the process disclosed in the specification of U.S. Pat. No. 3,965,207. The product was identified as ZSM-5 from its X-ray diffraction pattern. The product was calcined in an air atmosphere in an electric muffle furnace at 450° C. for 16 hours. Then, 20 g of the calcined product was treated in 200 cc of a 5% by weight aqueous solution of $NH_4Cl$ at 80° C. for 24 hours to perform ion-exchange. This treatment was repeated three times. The zeolite was then sufficiently washed with water, dried at 100° C., and then calcined in an air atmosphere at 450° C. for 16 hours in an electrical muffle furnace. The resulting zeolite had an Na content of 0.05% by weight. (The resulting product is referred to as catalyst A.)

(b) Preparation of Catalyst B $Pt(NH_3)_4Cl_2$ (0.052 g) was dissolved in 30 cc of water, and 10 g of the H-type ZSM-5 (catalyst A) obtained by the same method as in (a) was dipped in the aqueous solution at 50° C. for 8 hours to perform ion exchange. The powder was separated by filtration, washed fully with water, and dried at 100° C. for 8 hours in an electrical dryer and then at 200° C. for 16 hours. The resulting catalyst contained 0.27%, based on the total amount of the catalyst, of platinum. (This catalyst is referred to as catalyst B.)

(c) Preparation of Catalyst C $Pd(NH_3)_4Cl_2 \cdot H_2O$ (0.126 g) was dissolved in 30 cc of water, and 10 g of the catalyst A obtained by the same method as in (a) above was dipped in it, and then worked up in the same way as in the preparation of the catalyst B. The resulting catalyst contained 0.23% of palladium based on the total amount of the catalyst. (This catalyst is referred to as catalyst C.)

(d) Preparation of Catalyst D $RhCl_3 \cdot 3H_2O$ (0.076 g) was dissolved in 15 cc of water, and 10 g of the catalyst A obtained by the same method as in (a) above was dipped, and allowed to stand overnight at 80° C. With stirring, water was evaporated off. The product was heated at 200° C. for 4 hours, and then calcined in an air atmosphere in an electric muffle furnace at 450° C. for 16 hours. The resulting catalyst contained 0.30% of rhodium based on its total weight. (This catalyst is referred to as catalyst D.)

(e) Preparation of Catalyst E $IrCl_4$ (0.0174 g) was dissolved in 30 cc of water, and 10 g of the catalyst A obtained by the same method as in (a) above was dipped in it. Then, it was treated in the same way as in the preparation of catalyst D. The resulting catalyst contained 0.1% of iridium based on its total weight. (This catalyst is referred to as catalyst E.)

(f) Preparation of Catalyst F

A catalyst was prepared in the same way as in the preparation of catalyst B except that the amount of $Pt(NH_3)_4Cl_2$ was changed to 0.0173 g. The resulting catalyst contained 0.09%, based on its total weight, of platinum. (This catalyst is referred to as catalyst F.)

(g) Preparation of Catalyst G 0.32 g of $Ni(NO_3)_2$ was dissolved in 30 cc of water, and 10 g of H-form ZSM-5 (catalyst A) was dipped in the solution. Ion exchange was performed in it at 50° C. for 24 hours, and then with stirring, water was evaporated off. The zeolite was then heated at 200° C. for 4 hours, and then calcined in an air atmosphere in an electric muffle furnace at 450° C. for 16 hours. The resulting catalyst contained 1.0%, based on its total weight, of nickel. (This catalyst is referred to as catalyst G.)

EXAMPLE 2

Each of the catalysts A, B, C and D in powder form was fully mixed with chromatographic alumina gel in a weight ratio of 1:1, and molded into a size of 10 to 20 mesh. Each of the molded products was calcined in the air at 450° C. for 16 hours. Subsequently, except the molded article obtained from catalyst A, each of the molded products obtained from catalysts B, C and D was reduced in a hydrogen flow at 400° C. for 2 hours. Then, a feedstock of the composition shown in Table 1 consisting of alkyl-substituted aromatic hydrocarbons having at least 9 carbon atoms was subjected to hydro-dealkylation in a fixed bed flowing type reactor. The reaction conditions were as follows:

Reaction temperature: 380° C.
Weight hourly space velocity (WHSV): 3.0 $HR^{-1}$
Hydrogen/hydrocarbon mole ratio: 1:1
Reaction pressure: atmospheric pressure From 1 to 3 hours after the initiation of feeding, the resulting products had the compositions shown in Table 1.

It is seen from the results that catalysts B, C and D containing noble metals of Group VIII of the periodic table have superior selectivity of hydro-deethylation reaction, and give useful benzene and xylenes at high recovery ratios.

TABLE 1

|  | Composition of feedstock (wt. %) | Composition of the product (wt. %) | | | |
| --- | --- | --- | --- | --- | --- |
|  |  | Catalyst A (ZSM-5) | Catalyst B (Pt-ZSM-5) | Catalyst C (Pd-ZSM-5) | Catalyst D (Rh-ZSM-5) |
| $C_1$-$C_3$ paraffins |  | 11.9 | 14.7 | 13.9 | 13.6 |
| Benzene |  | 5.6 | 7.3 | 7.3 | 5.1 |
| Toluene |  | 5.0 | 12.9 | 13.0 | 12.0 |
| Ethylbenzene |  | 6.1 | 6.1 | 5.8 | 9.1 |
| Xylene |  | 8.5 | 9.5 | 9.7 | 9.5 |
| Ethyltoluene | 25.0 | 23.9 | 10.4 | 10.9 | 11.2 |
| Trimethylbenzene | 25.0 | 24.9 | 24.4 | 24.9 | 24.3 |
| Diethylbenzene | 25.0 | 2.5 | 2.2 | 1.9 | 2.4 |

TABLE 1-continued

| | Composition of feedstock (wt. %) | Composition of the product (wt. %) | | | |
|---|---|---|---|---|---|
| | | Catalyst A (ZSM-5) | Catalyst B (Pt-ZSM-5) | Catalyst C (Pd-ZSM-5) | Catalyst D (Rh-ZSM-5) |
| Ethylxylene | 25.0 | 13.0 | 12.6 | 12.6 | 12.8 |
| Yield (%) of aromatics | | 99.6 | 98.9 | 99.7 | 98.5 |
| Rate of decomposition of ET (%) | | 4.4 | 58.5 | 56.6 | 55.2 |
| Rate of decomposition of TMB (%) | | 0.4 | 2.5 | 0.4 | 3.0 |
| Rate of decomposition of DEB (%) | | 90.0 | 91.4 | 92.6 | 90.5 |
| Rate of decomposition of EX (%) | | 48.0 | 49.6 | 49.7 | 48.8 |
| $\Delta T/\Delta ET$ | | 5.90 | 1.1 | 1.2 | 1.1 |
| $(\Delta B + \Delta EB)/\Delta DEB$ | | 0.77 | 0.89 | 0.86 | 0.90 |
| $\Delta X/\Delta EX$ | | 0.89 | 0.97 | 0.99 | 0.98 |

$$\text{Yield of aromatics (\%)} = \frac{\text{Moles of the benzene rings of the product}}{\text{Moles of the benzene rings in the feedstock}} \times 100$$

$$\text{Rate of decomposition of ET (\%)} = \frac{ET_F - ET_P}{ET_F} \times 100$$

$$\text{Rate of decomposition of TMB (\%)} = \frac{TMB_F - TMB_P}{TMB_F} \times 100$$

$$\text{Rate of decomposition of DEB (\%)} = \frac{DEB_F - DEB_P}{DEB_F} \times 100$$

$$\text{Rate of decomposition of EX (\%)} = \frac{EX_F - EX_P}{EX_F} \times 100$$

The various abbreviations used above have the following meanings.
ET: ethyltoluene
TMB: trimethylbenzene
DEB: diethylbenzene
EX: ethylxylene
Suffix F: feed
Suffix P: product $\Delta T/\Delta ET$: the mole ratio of toluene formed to ethyltoluene decomposed $(\Delta B + \Delta EB)/\Delta DEB$: the mole ratio of benzene and ethylbenzene formed to diethylbenzene decomposed $\Delta X/\Delta EX$: the mole ratio of xylene formed to ethylxylene decomposed

EXAMPLE 3

Using each of the catalysts A and B used in Example 2, hydro-dealkylation reaction was performed, and variations in the composition of the product were traced periodically. The reducing treatment and reaction conditions were the same as in Example 2 except that the temperature was changed to 410° C. The results are shown in Table 2.

It is seen from the results shown in Table 2 that the reduction in activity with time of the catalyst B is smaller than that of the catalyst A, and the selectivity of catalyst B for hydro-deethylation reaction is higher than that of catalyst A.

TABLE 2

| | Composition of feedstock (wt. %) | Composition of the product (wt. %) | | | | | |
|---|---|---|---|---|---|---|---|
| | | Catalyst A | | | Catalyst B | | |
| | | Hr 1~3 | Hr 15~17 | Hr 41~43 | Hr 1~3 | Hr 23~25 | Hr 47~49 |
| $C_1$–$C_5$ paraffins | | 15.1 | 13.1 | 8.8 | 16.3 | 15.2 | 13.5 |
| Benzene | | 8.0 | 6.9 | 2.7 | 8.8 | 8.5 | 7.7 |
| Toluene | | 13.2 | 11.1 | 7.9 | 14.8 | 14.2 | 13.4 |
| Ethylbenzene | | 3.9 | 5.6 | 9.0 | 4.1 | 5.4 | 6.1 |
| Xylene | | 9.3 | 7.6 | 6.5 | 9.6 | 7.9 | 7.3 |
| Ethyltoluene | 25.0 | 14.2 | 14.7 | 15.6 | 8.7 | 7.8 | 8.7 |
| Trimethylbenzene | 25.0 | 23.6 | 24.0 | 24.8 | 23.9 | 24.3 | 24.9 |
| Diethylbenzene | 25.0 | 1.4 | 3.1 | 8.0 | 1.4 | 2.1 | 2.8 |
| Ethylxylene | 25.0 | 11.3 | 13.9 | 16.7 | 12.4 | 14.6 | 15.6 |
| Yield of aromatics (%) | | 99.0 | 99.0 | 99.7 | 98.5 | 98.9 | 99.8 |
| Rate of decomposition of ET (%) | | 43.1 | 41.2 | 37.8 | 65.1 | 69.0 | 65.3 |
| Rate of decomposition of TMB (%) | | 5.7 | 4.0 | 1.0 | 4.6 | 3.0 | 2.5 |
| Rate of decomposition of DEB (%) | | 94.3 | 87.5 | 68.2 | 94.4 | 91.8 | 88.8 |
| Rate of decomposition of EX (%) | | 55.0 | 44.4 | 33.1 | 50.5 | 41.8 | 37.7 |
| $\Delta T/\Delta ET$ | | 1.60 | 1.41 | 1.09 | 1.18 | 1.08 | 1.07 |
| $(\Delta B + \Delta EB)/\Delta DEB$ | | 0.79 | 0.86 | 0.94 | 0.86 | 0.94 | 0.94 |
| $\Delta X/\Delta EX$ | | 0.85 | 0.87 | 0.88 | 0.96 | 0.96 | 0.98 |

EXAMPLE 4

Catalyst B prepared in Example 1 was molded in the same way as in Example 2, and subsequently calcined and reduced under the same conditions as in Example 2. Then, using a fixed bed flow reactor, n-propylbenzene was hydro-dealkylated in the presence of the resulting catalyst under the following reaction conditions.

Pressure: 0 psig
Temperature: 400° C.
$H_2$/n-propylbenzene mole ratio: 2:1
WHSV: 3 $hr^{-1}$ The composition of the resulting product, the conversion, the selectivity for benzene, and selectivity for propane were as follows:

| Composition of the product (% by weight) | |
|---|---|
| Methane | 0.02 |
| Ethane | 1.48 |
| Propane | 28.17 |
| Butane | 3.09 |
| Paraffins with at least 5 carbons | 0.24 |
| Benzene | 59.85 |
| Toluene | 2.58 |
| $C_8$ aromatic hydrocarbons | 1.73 |
| $C_9$ aromatic hydrocarbons | 0.82 |
| Aromatic hydrocarbons with at least 10 carbons | 2.00 |
| Conversion | 99.2% |
| Selectivity for benzene | 92.8% |
| Selectivity for propane | 77.6% |

As is seen from the results obtained, when n-propylbenzene is de-propylated in the presence of catalyst B under the reaction conditions in accordance with this invention, in spite of the very high conversion of n-propylbenzene, the formation of by-products, toluene, xylene and $C_{10}$ aromatics, is reduced, and the selectivity for benzene is very high.

In addition, formation of propane from the propyl group split off by the depropylation proceeds selectively, and the amounts of methane, ethane, butane or higher paraffins as by-products which may be formed by the secondary dealkylation and alkylation of the propyl group are extremely small.

The selectivity for benzene and the selectivity for propane were calculated from the following equations.

$$\text{Selectivity for benzene} = \frac{\text{Moles of benzene formed}}{\text{Moles of n-propylbenzene converted}} \times 100$$

$$\text{Selectivity for propane} = \frac{\text{Moles of propane formed}}{\text{Moles of n-propylbenzene converted}} \times 100$$

EXAMPLE 5

Using an aromatic hydrocarbon material having a high ethyl group content and the composition shown below, the effect of de-ethylation under the reaction conditions of this invention was examined.

Each of the catalyst B (containing platinum), catalyst A (H-form ZSM-5), and catalyst G (containing nickel) was molded in the same way as in Example 2, and subsequently, calcined and treated under the same reducing conditions as in Example 2. Then, the hydrocarbon material was hydrogenatingly de-ethylated in the presence of each of the catalysts used in a fixed bed flow reactor under the reaction conditions shown below.

Reaction conditions
Pressure: 0 psig
Temperature: 400° C.
$H_2$/aromatic hydrocarbons mole ratio: 2:1
WHSV: 3 $HR^{-1}$

| Composition of the starting hydrocarbon material (% by weight) | |
|---|---|
| Cumene | 0.9 |
| Ethyltoluene | 9.0 |
| Trimethylbenzene | 10.0 |
| Diethylbenzene | 47.0 |
| Ethylxylene | 33.1 |

Results

The composition (% by weight) of each of the resulting products is shown in Table 3 together with other data.

TABLE 3

| | | Catalyst B Pt-containing ZSM-5 | Catalyst A H-form ZSM-5 | Catalyst G Ni-containing ZSM-5 |
|---|---|---|---|---|
| Composition (% by weight) of the products | $CH_4$ | 0.01 | 0.09 | 1.78 |
| | $C_2H_6$ | 24.69 | 3.37 | 12.47 |
| | $C_2H_4$ | 0.02 | 3.14 | 0.81 |
| | $C_3H_8$ | 0.59 | 6.68 | 4.20 |
| | $C_4H_{10}$ | 0.04 | 5.75 | 1.99 |
| | Paraffins with $C_5$ or more | — | 0.19 | 0.03 |
| | Benzene | 23.62 | 12.34 | 12.74 |
| | Toluene | 8.72 | 8.92 | 8.64 |
| | Ethylbenzene | 3.09 | 11.61 | 11.97 |
| | Xylenes | 16.55 | 10.92 | 13.90 |
| | Cumene | 0 | 1.08 | 1.04 |
| | Ethyltoluene | 0.45 | 4.17 | 3.88 |
| | Trimethylbenzene | 9.52 | 8.66 | 8.91 |
| | Diethylbenzene | 0.52 | 4.84 | 3.29 |
| | Ethylxylene | 12.18 | 18.24 | 14.35 |
| ΔT/ΔET | | 1.33 | 2.41 | 2.2 |
| Δ(B + EB)/ΔDEB | | 0.957 | 0.851 | 0.847 |
| ΔX/ΔEX | | 0.999 | 0.929 | 0.937 |
| ΔEB/Δ(EB + X) | | 0.157 | 0.515 | 0.463 |
| $C_2H_6$ in products having 4 or less carbons (mole %) | | 98.1 | 23.4 | 60.4 |

When the data for catalyst B in accordance with this invention are compared with those for catalysts A and G, the following conclusion can be drawn with regard to catalyst B.

(1) De-ethylation reaction is fast, and de-ethylation of ethyltoluene is especially remarkable.

(2) The proportion of ethane in the resulting products (with not more than 4 carbon atoms) is high, and ethane forms almost quantitatively. Furthermore, the amounts of alkanes having at least 3 carbon atoms, are small. This shows that the formation of alkanes having at least 3 carbon atoms by the alkyl-exchange and secondary reaction of the ethyl group is inhibited by the noble metal. This is presumably because the noble metals have higher activity of hydrogenating the ethyl group than other metals, and thus, de-ethylation reaction is based on the inherent properties of the noble metals.

(3) Xylene forms substantially quantitatively from ethylxylene. Ethylbenzene obtained by converting one ethyl group of diethylbenzene is further de-ethylated. As a result, the concentration of ethylbenzene in the product is low, and therefore, the concentration of ethylbenzene in the recovered $C_8$ aromatics obtained by separating the resulting $C_6$–$C_8$ aromatics is low. The products are therefore suitable as a starting material for the manufacture of p-xylene and/or o-xylene.

(4) Formation of toluene is due to the de-ethylation of ethyltoluene. The amount of toluene which is formed by the demethylation of feed materials other than ethyltoluene is small.

EXAMPLE 6

Each of catalysts E and G prepared in Example 1 was molded in the same way as in Example 2, and subsequently, calcined and reduced under the same conditions as in Example 2. Ethylbenzene was hydrogenatingly de-ethylated in the presence of each of the catalysts in a fixed bed flow reactor. The reaction conditions and the compositions of the products were as shown in Table 4.

TABLE 4

|  | Catalyst E (Ir-ZSM5) | Catalyst G (Ni-ZSM5) |
| --- | --- | --- |
| Temperature (°C.) | 350 | 350 |
| Pressure | atmospheric | atmospheric |
| $H_2$/HC mole ratio | 0.91 | 0.88 |
| WHSV | 6.0 | 6.0 |
| Reaction time (hours) | 17–19 | 1–3 |
| Conversion of ethylbenzene (%) | 36.13 | 33.71 |
| ($\Delta$B – DEB)/$\Delta$EB (*) | 75.67 | 26.95 |
| $C_1$ | 0.19 | — |
| $C_2$ | 7.54 | 1.87 |
| $C_3$ | 0.03 | 0.40 |
| $C_4$ | — | 0.23 |
| Benzene | 22.94 | 15.51 |
| Toluene | 0.09 | 0.08 |
| Ethylbenzene | 63.87 | 66.29 |
| $C_8$ aromatic hydrocarbons | 0.18 | 0.17 |
| $C_9$ aromatic hydrocarbons | 0.32 | 0.30 |
| Aromatic hydrocarbons having at least 10 carbons | 4.85 | 15.16 |

(*): ($\Delta$B – $\Delta$DEB)/$\Delta$EB is the percentage of the (amount of benzene formed minus the amount of diethylbenzene formed) based on the amount of ethylbenzene fed. This represents the selectivity of the hydro-deethylation of ethylbenzene.

It is seen from Table 4 that when ZSM-5 catalyst containing iridium (catalyst E) is used, the selectivity of de-ethylation reaction is very high and the amount of ethane formed is large as compared with the case of using ZSM-5 containing nickel (catalyst G).

EXAMPLE 7

This Example shows the effect of the reaction pressure.

The catalyst B prepared in Example 1 was molded in the same way as in Example 2, and subsequently, calcined and reduced under the same conditions as in Example 2. Then, the same material as used in Example 2 was fed into a fixed bed flow reactor under the conditions shown in Table 5. The amounts of naphthenes having 6 carbon atoms in the resulting products were examined. The results are shown in Table 5.

TABLE 5

|  | IV | V | VI | VII |
| --- | --- | --- | --- | --- |
| Reaction temperature (°C.) | 400 | 400 | 400 | 450 |
| $H_2$/starting material mole ratio | 2:1 | 2:1 | 4:1 | 8:1 |
| WHSV (hr$^{-1}$) | 3 | 3 | 3 | 3 |
| Reaction pressure (psig) | 0 | 75.3 | 135.3 | 284 |
| Amount (wt. %) of $C_6$ naphthenes in the products | 0 | 0.020 | 0.34 | 0.42 |
| Benzene (wt. %) in the products | 23.81 | 23.24 | 23.31 | 12.9 |
| $C_6$ naphthene/benzene mole ratio | — | 0.00083 | 0.0147 | 0.0324 |

The following conclusions can be drawn from the data shown in Table 5.

To produce benzene as a final product without a purification step such as extraction, the amount of $C_6$ naphthenes in the resulting benzene is desirably not more than 0.2%. To achieve it, the pressure is desirably not more than 100 psig.

EXAMPLE 8

In this Example, the effect of the proportion of the noble metal on the dealkylation reaction was examined.

In the preparation of catalyst B in Example 1, the amount of Pt(NH$_3$)$_4$Cl$_2$ used was varied to form ZSM-5 catalysts having a platinum content of 0.005% by weight, 0.01% by weight, 0.05% by weight, and 0.1% by weight, respectively.

Each of these catalysts was molded in the same way as in Example 2, and subsequently, calcined and reduced under the same conditions as in Example 2. Then, a material having the following composition was fed into a fixed bed flow reactor under the following conditions. The amount of naphthenes having at least 6 carbon atoms, and the selectivity for de-ethylation of ethylbenzene were determined, and are shown in Table 6.

| Composition of the starting material (% by weight) | |
| --- | --- |
| Ethylbenzene | 15 |
| Mixture of three xylene isomers | 84.5 |
| Toluene | 0.5 |

| Reaction conditions | |
| --- | --- |
| Reaction pressure | 105 psig |
| Temperature | 350° C. |
| $H_2$/starting material | 3:1 (mole ratio) |
| WHSV | 8 hr$^{-1}$ |

TABLE 6

|  | Run No. | | | |
| --- | --- | --- | --- | --- |
|  | 8-1 | 8-2 | 8-3 | 8-4 |
| Platinum content of the catalyst (wt. %) | 0.005 | 0.01 | 0.05 | 0.1 |
| Concentration of naphthenes having at least 6 carbon atoms in the products (wt. %) | 0.214 | 0.12 | 1.98 | 1.93 |

TABLE 6-continued

| | Run No. | | | |
|---|---|---|---|---|
| | 8-1 | 8-2 | 8-3 | 8-4 |
| Selectivity for de-ethylation of ethylbenzene (%)* | 82.2 | 90.0 | 88.0 | 85.0 |

(*) Calculated in accordance with the following equation.

$$\frac{\text{Weight of de-ethylated ethylbenzene}}{\text{Weight of ethylbenzene that disappeared}} \times 100$$

The following conclusions can be drawn from the results shown in Table 6.

The effect of hydro-deethylation reaction by platinum appears even when the amount of platinum is as small as 0.005% by weight. The de-ethylating ability of the catalyst scarcely changes even when the concentration of platinum increases. Rather, the hydrogenation of the benzene ring is promoted to form naphthenes having 6 to 8 carbon atoms. Accordingly, the concentration of the noble metal is desirably small. However, when the concentration of the noble metal exceeds a certain limit (0.05% by weight), the ability of the catalyst to hydrogenate the benzene ring reaches saturation. Accordingly, from the economical viewpoint alone, high concentrations of the noble metal are not desirable.

EXAMPLE 9

In this Example, the effect of the reaction temperature was examined.

The catalyst C prepared in Example 1 was molded in the same way as in Example 2, and subsequently calcined and reduced under the same conditions as in Example 2. Then, the same reaction as in Example 2 was carried out in a fixed bed flow reactor except that the reaction temperature was varied.

The selectivity of xylenes from ethylxylene ($\Delta X/\Delta EX$), and the amounts of benzene and toluene in the products ($\Delta B$ and $\Delta T$) were examined, and the results are shown in Table 7.

TABLE 7

| | Run No. | | | |
|---|---|---|---|---|
| | 9-1 | 9-2 | 9-3 | 9-4 |
| Reaction temperature (°C.) | 350 | 380 | 410 | 450 |
| $\Delta X/\Delta EX$ | 1.05 | 0.99 | 0.97 | 0.88 |
| $\Delta B$ (wt. %) | 5.4 | 7.3 | 8.1 | 9.7 |
| $\Delta T$ (wt. %) | 11.7 | 13.0 | 14.4 | 16.7 |

It is seen from the results shown in Table 7 that when the reaction temperature exceeds about 450° C., the resulting toluene and xylene undergo demethylation reaction, and the amounts of benzene and toluene formed increase abruptly and therefore, that this approaches a conventional dealkylating technique.

EXAMPLE 10

In this Example, the effect of weight hourly space velocity (WHSV) was examined.

The catalyst B prepared in Example 1 was molded in the same way as in Example 2, and subsequently, calcined and reduced under the same conditions as in Example 2. Then, the same reaction as in Example 2 was performed in a fixed bed flow reactor except that WHSV was varied.

The conversion of diethylbenzene (DEB) and the conversion of ethylxylene (EX) were examined, and the results are shown in Table 8.

TABLE 8

| | Run No. | | | | | |
|---|---|---|---|---|---|---|
| | 10-1 | 10-2 | 10-3 | 10-4 | 10-5 | 10-6 |
| WHSV (hr$^{-1}$) | 1 | 3 | 5 | 8 | 12 | 20 |
| Conversion (%) of DEB | 97 | 91.4 | 90.5 | 84.5 | 74 | 58 |
| Conversion (%) of EX | 60.2 | 49.6 | 33.0 | 24.0 | 18 | 8 |

It is seen from Table 8 that as the WHSV increases, the conversions of DEB and EX abruptly decrease, and at a WHSV of at least 15, the conversions are low and not commercially feasible.

What we claim is:

1. In a process for dealkylating a hydrocarbon material containing at least one alkyl-substituted aromatic hydrocarbon having bonded to the aromatic ring at least one alkyl group with at least 2 carbon atoms in the gaseous phase in the presence of hydrogen using a hydro-dealkylation catalyst, the improvement wherein (a) said hydro-dealkylation catalyst in composed of a crystalline aluminosilicate having high acid activity, having a silica/alumina mole ratio of from 20 to 200, and containing a noble metal selected from platinum, palladium, rhodium and iridium, and (b) said dealkylation is carried out at a temperature of 250° C. to 420° C. and a pressure of not more than 100 psig, with the provisos that when the noble metal is platinum, said noble metal is present in the catalyst in an amount of from 0.001 to 0.5% by weight and when the noble metal is palladium, rhodium or iridium, said noble metal is present in the catalyst in an amount of from 0.001 to 2% by weight, based on the weight of the aluminosilicate, thereby selectively removing said alkyl group containing at least 2 carbon atoms from said alkyl-substituted aromatic hydrocarbon with substantial inhibition of the hydrogenation of the aromatic ring.

2. The process of claim 1 wherein said crystalline aluminosilicate has a silica/alumina mole ratio of 30 to 150.

3. The process of claim 1 wherein said crystalline aluminosilicate is zeolite ZSM-5.

4. The process of claim 1 wherein said catalyst contains 0.005 to 1% by weight, based on said crystalline aluminosilicate, of said noble metal.

5. The process of claim 1 wherein said dealkylation is carried out at a temperature of 320° C. to 410° C.

6. The process of claim 1 wherein said dealkylation is carried out under a pressure of 0 to 90 psig.

7. The process of claim 1 wherein said hydrocarbon material is fed at a weight hourly space velocity of about 0.1 to about 20.

8. The process of claim 1 wherein said hydrocarbon material and hydrogen are fed so that the mole ratio of hydrogen to hydrocarbon material is from 0.5 to 10.

9. The process of claim 1 wherein said alkyl-substituted aromatic hydrocarbon is an aromatic hydrocarbon having bonded to the aromatic ring 1 to 3 linear or branched alkyl groups with 2 to 4 carbon atoms and optionally having 1 to 5 methyl groups bonded to the aromatic ring.

10. The process of claim 9 wherein said alkyl-substituted aromatic hydrocarbon is selected from the group consisting of ethylbenzene, ethyltoluene, diethylbenzene, ethylxylene, n-propylbenzene, cumene and cymene.

11. The process of claim 1 wherein said hydrocarbon material comprises a mixture of said alkyl-substituted aromatic hydrocarbon and a methyl-substituted aromatic hydrocarbon.

12. The process of claim 11 wherein said hydrocarbon material contains at least 80% by weight of said mixture of aromatic hydrocarbons.

13. The process of claim 11 wherein said methyl-substituted aromatic hydrocarbon is a methyl-substituted benzene having 1 to 5 methyl groups bonded to the benzene ring.

14. The process of claim 1 wherein said hydrocarbon material contains at least 30% by weight of said alkyl-substituted aromatic hydrocarbon.

15. The process of claim 1 wherein said catalyst comprises 1 to 99% by weight the crystalline aluminosilicate.

* * * * *